(12) United States Patent
Jerebko (10) Patent No.: US 8,611,492 B2
(45) Date of Patent: Dec. 17, 2013

(54) IMAGING METHOD FOR ROTATING A TISSUE REGION

(75) Inventor: Anna Jerebko, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 7 days.

(21) Appl. No.: 13/357,995

(22) Filed: Jan. 25, 2012

(65) Prior Publication Data

US 2012/0189091 A1 Jul. 26, 2012

(30) Foreign Application Priority Data

Jan. 25, 2011 (DE) .......................... 10 2011 003 135

(51) Int. Cl.
*A61B 6/04* (2006.01)
*A61B 6/00* (2006.01)

(52) U.S. Cl.
USPC .............................................. 378/37; 378/22

(58) Field of Classification Search
USPC ................................. 378/4, 22, 37
See application file for complete search history.

(56) References Cited

U.S. PATENT DOCUMENTS

| 4,882,679 | A | * | 11/1989 | Tuy et al. ...................... 600/425 |
| 5,371,778 | A | * | 12/1994 | Yanof et al. ........................ 378/4 |
| 5,722,408 | A | * | 3/1998 | Dehner et al. ................ 600/407 |
| 5,986,662 | A | * | 11/1999 | Argiro et al. .................. 345/424 |
| 7,945,014 | B2 | | 5/2011 | Mertelmeier |
| 7,965,812 | B2 | | 6/2011 | Hanke et al. |
| 2002/0176530 | A1 | * | 11/2002 | Okumura et al. ............... 378/19 |
| 2004/0091084 | A1 | * | 5/2004 | Griffith ......................... 378/210 |
| 2004/0228453 | A1 | * | 11/2004 | Dobbs et al. .................. 378/210 |
| 2005/0020902 | A1 | * | 1/2005 | Janes ............................ 600/407 |
| 2005/0102315 | A1 | * | 5/2005 | Krishnan ...................... 707/102 |
| 2008/0123930 | A1 | * | 5/2008 | Bernard et al. ............... 382/132 |
| 2008/0226018 | A1 | | 9/2008 | Partain et al. |
| 2009/0034684 | A1 | | 2/2009 | Bernard et al. |
| 2009/0080752 | A1 | | 3/2009 | Ruth et al. |
| 2009/0310844 | A1 | | 12/2009 | Ludwig et al. |
| 2010/0034450 | A1 | | 2/2010 | Mertelmeier |
| 2010/0166267 | A1 | | 7/2010 | Zahng et al. |
| 2011/0122992 | A1 | | 5/2011 | Hanke et al. |

FOREIGN PATENT DOCUMENTS

| DE | 102006046741 A1 | 4/2008 |
| DE | 102008004473 A1 | 7/2009 |
| DE | 102008028387 A1 | 12/2009 |
| DE | 102008033150 A1 | 2/2010 |
| EP | 2138098 A1 | 12/2009 |

OTHER PUBLICATIONS

Long et al., "A 3D Forward and Back-Projection Method for X-Ray CT Using Separable Footprint", Proceedings of 10th Fully 3D Meeting and 2nd HPIR Workshop, Sep. 5-10, 2009, Beijing, China, pp. 146-149.

(Continued)

*Primary Examiner* — Alexander H Taningco
(74) *Attorney, Agent, or Firm* — Laurence A. Greenberg; Werner H. Stemer; Ralph E. Locher (57) ABSTRACT

An imaging method, more particularly a mammography method, includes rotating a tissue region in the virtual domain. Projection recordings of a tissue region are generated by way of radiation emitted by an emitter, which radiation is captured by a detector after passing through the tissue region. Slice images are generated from the projection recordings. A slice image region corresponding to a partial tissue region is rotated virtually. The virtually rotating partial tissue region can be displayed as a set of virtual projections.

13 Claims, 5 Drawing Sheets

(56) References Cited

OTHER PUBLICATIONS

Schretter, "A fast tube of response ray-tracer", PET/Cyclotron Unit, Universite Libre de Bruxelles, Belgium, Med. Phys., 33 (12), Dec. 2006, pp. 4744-4747.

Joseph, "An Improved Algorithm for Reprojecting Rays Through Pixel Images", IEEE Transactions on Medical Imaging, Vo. MI-1, No. 3, Nov. 1982, pp. 192-196.

De Man et al., "Distance-driven projection and backprojection in three dimensions", Phys. Med. Biol. 49, 2004, pp. 2463-2475.

Siddon, "Fast calculation of the exact radiological path for a three-dimensional CT array", Med. Phys. 12 (2), Mar./Apr. 1985, pp. 252-255.

Matej et al., "Practical Considerations for 3-D Image Reconstruction Using Spherically Symetric Volume Elements", IEEE Transactions on Medical Imaging, vol. 15, No. 1, Feb. 1996, pp. 68-78.

Ridell et al., "Rectification for Cone-Beam Projection and Backprokection", IEEE Transactions on Medical Imaging, vol. 25, No. 7, Jul. 2006.

Ziegler et al., "Efficient projection and backprojection scheme for sherically symetric basis functions in divergent beam geometry", Med. Phys. 33 (12), Dec. 2006, pp. 4653-4663.

Oppelt, "Imaging Systems for Medical Diagnostics", 2005, ISBN: 3-89578-226-2, pp. 47-48.

\* cited by examiner

IMAGING METHOD FOR ROTATING A TISSUE REGION

CROSS-REFERENCE TO RELATED APPLICATION

This application claims the priority, under 35 U.S.C. §119, of German patent application DE 10 2011 003 135.9, filed Jan. 25, 2011; the prior application is herewith incorporated by reference in its entirety.

BACKGROUND OF THE INVENTION

Field of the Invention

The present invention relates to an imaging method, more particularly a mammography method, in which a simulated volume that represents a tissue region is rotated.

In a tomosynthesis method, a three-dimensional image is generated from a plurality of two-dimensional projections. An X-ray apparatus with an X-ray beam source and a detector is used to generate a first two-dimensional image or a first projection of the tissue to be examined, through which tissue the X-ray beam passes. Here, the two-dimensional image represents the attenuation of the X-ray radiation by the tissue in the volume or in the breast. A second two-dimensional image or a second projection of the same tissue or volume is recorded after the beam source and/or the detector was moved into a second position. After a plurality of two-dimensional images were recorded, a three-dimensional tomosynthesis image can be generated by means of a reconstruction.

Mammography is a field of application of the three-dimensional imaging method mentioned above. An image generation device typically used in mammography comprises a pivotable X-ray beam source and a stationary X-ray detector. The tissue to be examined is positioned over the stationary detector, with the tissue to be examined being compressed and not being in a natural shape. The X-ray source is subsequently pivoted over a number of steps or continuously, for example within a range of +/−25°, and the stationary detector is used to record a plurality of two-dimensional X-ray images from different pivot positions of the X-ray beam source. It goes without saying that it is also possible to use a plurality of stationary X-ray beam sources or to merely displace the X-ray beam source in a translational fashion. It is also possible for the detector to be displaced or pivoted counter to the movement of the X-ray source. In the case of craniocaudal recordings, the X-ray beam source(s) emit(s) X-ray beams from positions that are arranged along a line running parallel to the axis running from shoulder to shoulder of a patient. A beam path parallel to the chest wall can result in the entire tissue of the breast being imaged and the thorax not being irradiated. A three-dimensional image is generated from the plurality of two-dimensional X-ray images by means of the reconstruction.

Pertinent prior art imaging methods and devices for mammography are described, for example, in the following commonly assigned patents and published patent applications: U.S. Pat. No. 7,945,014 B2 and DE 10 2006 046 741 A1; US 2010/0034450 A1 and DE 10 2008 004 473 A1; US 2011/0122992 A1 and DE 10 2008 033 150 A1; U.S. Pat. No. 7,965,812 B2 and EP 2 138 098 A1; and US 2009/0310844 A1 and DE 10 2008 028 387 A1.

In the prior art, so-called filtered back projections, iterative reconstructions or algebraic reconstructions are used to reconstruct a three-dimensional image from a plurality of two-dimensional images; by way of example, these filtered back projections are described in chapter 10.5 of Imaging Systems for Medical Diagnostics, Arnulf Oppelt, Publicis Corporate Publishing, Erlangen, ISBN 3-89578-226-2. These filtered back projection reconstruction methods display reconstructed images with a comparatively high contrast and comparatively great detail, but lose information in respect of the relative tissue density in the case of tomosynthesis with a restricted scanning angle as a result of the missing data. This is the result of certain filter kernels removing low-frequency components. In general, digital breast tomosynthesis (DBT) is afflicted by incomplete data and poor quantum statistics, which is restricted by the overall dose absorbed in the breast. The breast mainly consists of glandular tissue, fatty tissue, connective tissue and blood vessels. The X-ray attenuation coefficients of these types of tissue are very similar, making the evaluation of three-dimensional mammography images significantly harder. The main field of application of imaging methods in mammography is the early detection of cancerous tissue. This is made more difficult by the fact that cancerous tissue has a similar X-ray attenuation coefficient to other types of tissue.

By way of example, mammography methods are described in chapter 12.6 of Imaging Systems for Medical Diagnostics, Arnulf Oppelt, Publicis Corporate Publishing, Erlangen, ISBN 3-89578-226-2.

In the prior art, a so-called slab MIP (slab maximum intensity projection), an average intensity projection rendering, a multiple planar reconstruction (MRP), a maximum intensity projection (MIP) or simply a generated two-dimensional mammography image, which was generated from the tomosynthesis projection images and/or from the reconstructed tomosynthesis image data, is used for visualizing tomosynthesis data. As a result of the density of the data and the occlusion resulting therefrom, these techniques are not always optimal for analyzing soft-tissue data. High density soft tissue can only be visualized by removing the occluding low density soft tissue, for example by means of an opacity transfer function. It follows that the low density tissue, which provides important context information for the features with a high density, is no longer present in the visualization. This is undesirable when examining soft tissue because the soft-tissue contrast provides the main source of information for diagnosing tissue changes.

SUMMARY OF THE INVENTION

It is accordingly an object of the invention to provide an imaging process which overcomes the above-mentioned disadvantages of the heretofore-known devices and methods of this general type and which provides for an improved display of a tissue region in that a tissue volume is imaged such that a tissue change can be identified in an improved manner.

With the foregoing and other objects in view there is provided, in accordance with the invention, an imaging method, which comprises:

generating projection recordings of a tissue region by way of radiation emitted by an emitter, the radiation being captured by a detector after passing through the tissue region;

generating slice images from the projection recordings; and rotating a slice image portion corresponding to a partial tissue region.

In other words, the objects of the invention are achieved by an imaging method which generates projection recordings of a tissue region by way of radiation emitted by an emitter, which radiation is captured by a detector after passing through the tissue. Slice images are generated from the projection recordings. A slice image portion corresponding to a partial tissue region is rotated in the virtual domain. The rotation may be brought about in a virtually continuous or stepwise fashion, wherein, optionally, respectively one step is carried out after an actuation by a user.

During the rotation, the rotational axis is preferably situated between the emitter and the detector. The radiologist can select the rotational axis such that a tissue change is displayed as clearly and with as much contrast as possible. The rotary axis may be fixed and the angle of rotation may be restricted to the angular range from the tomosynthesis.

Slice images may be generated by means of a back projection, more particularly a filtered back projection, iterative reconstruction or algebraic reconstruction. The slice image region corresponding to a partial tissue region may be rotated by means of a forward projection.

The step of rotating a slice image portion corresponding to a partial tissue region may generate projection images. The step of rotating a slice image region corresponding to a partial tissue region may generate projection images by means of simulated movement of the X-ray emitter and/or simulated movement of the X-ray detector.

Projection representations are created from the slice image region, which projection representations represent the attenuation of an X-ray beam when an X-ray beam passes through a tissue region. Since the simulated X-ray beam can pass through the tissue change over a particularly long path, this results in a particularly high (virtual) attenuation of the X-ray beam. The rotational axis can pass through the rotational axis of the X-ray source. As a result, a tissue change in the simulated projection recording can be displayed in a particularly clear fashion and with a particularly large amount of contrast. The projections can be generated using Siddon's method, Joseph's method, the distance driven projector, the separable footprint projector or by means of another ray-casting method or another forward-projection technique.

As an alternative to this, slice images corresponding to the respective rotational angle can be generated during the rotation.

During the step of rotating a slice image region corresponding to a partial tissue region, the rotational angle is substantially restricted to the rotational angle about which the real emitter and/or the real detector are pivoted during the step of generating the projection recordings of the tissue region. This affords the possibility of largely avoiding artifacts.

In accordance with a further feature of the invention, the method can furthermore include the step of selecting the slice image region that should be rotated. The user can select the region that should be rotated by means of selecting a window or a zoom window. The user can, in a slice image representation, select the region that should be rotated.

The imaging method can rotate the slice image region over a range of discrete rotational angles in order to generate a set of rotation views. The rotation views can be rotated slice images or projection views. The set of rotation views can be stored in a memory. The memory is preferably a non-volatile memory, for example a hard disk. This makes it possible to pre-calculate the rotating three-dimensional mammogram before visualization on a monitor. The rotation view is read out of the memory as soon as the radiologist wishes to display the rotation view. This allows a rotating three-dimensional mammogram with the rotation views also to be displayed within a short period of time on imaging devices with a comparatively low performance. Furthermore, multiple calculations are avoided when the radiologist switches back and forth between two rotation views with different rotational angles. The term rotation view comprises both a slice image and a projection image.

In a preferred implementation of the invention, the imaging method is a mammography method.

The invention also discloses a rotation apparatus which is designed to carry out the above-described method. The rotation apparatus can be a programmable computer or an apparatus constructed from discrete components.

The invention also discloses an imaging system with the rotation apparatus.

Furthermore, the invention relates to a computer program product that is stored in non-transitory form and which can be, or is, loaded into a memory of a computer and comprises executable instructions designed to carry out the above-described method.

Other features which are considered as characteristic for the invention are set forth in the appended claims.

Although the invention is illustrated and described herein as embodied in an imaging method for rotating a tissue region, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The invention will be explained below with reference to mammography. It is understood that the invention is applicable in other fields.

Figure 1:
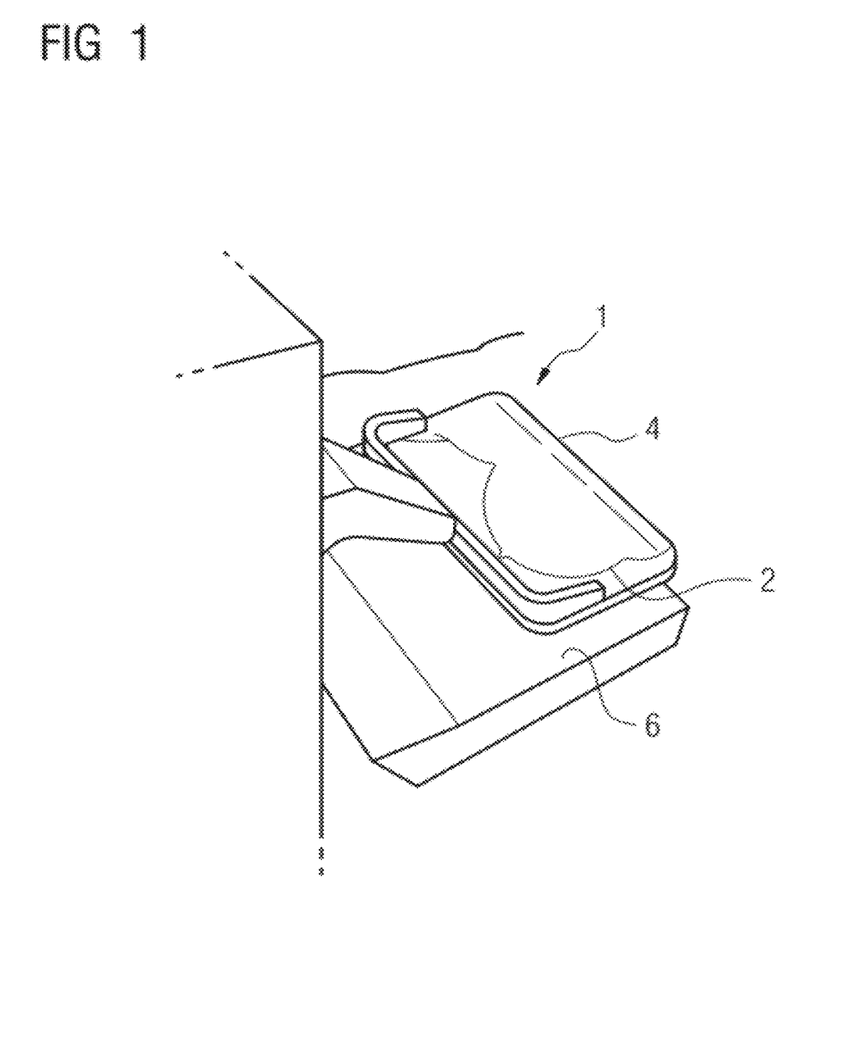
FIG. 1 shows a modality, in which the breast is compressed in order to carry out recordings of the interior of the breast.

Referring now to the figures of the drawing in detail and first, particularly, to FIG. 1 thereof, there is shown a first imaging modality, which has a compression plate 4 and a compression table 6, between which the breast 2 is clamped. The breast is usually compressed in this fashion until a predetermined compression force is reached. A plurality of X-ray sources or at least one movable X-ray source (not illustrated) can be arranged over the compression plate 4. An X-ray detector can be arranged in or below the table 6. This device can be used to capture projections from different directions by means of X-ray radiation, from which, as described at the outset, it is possible to generate slice images.

The compressed breast is captured in the mediolateral oblique (MLO) position in the first imaging modality 1.

Figure 2:
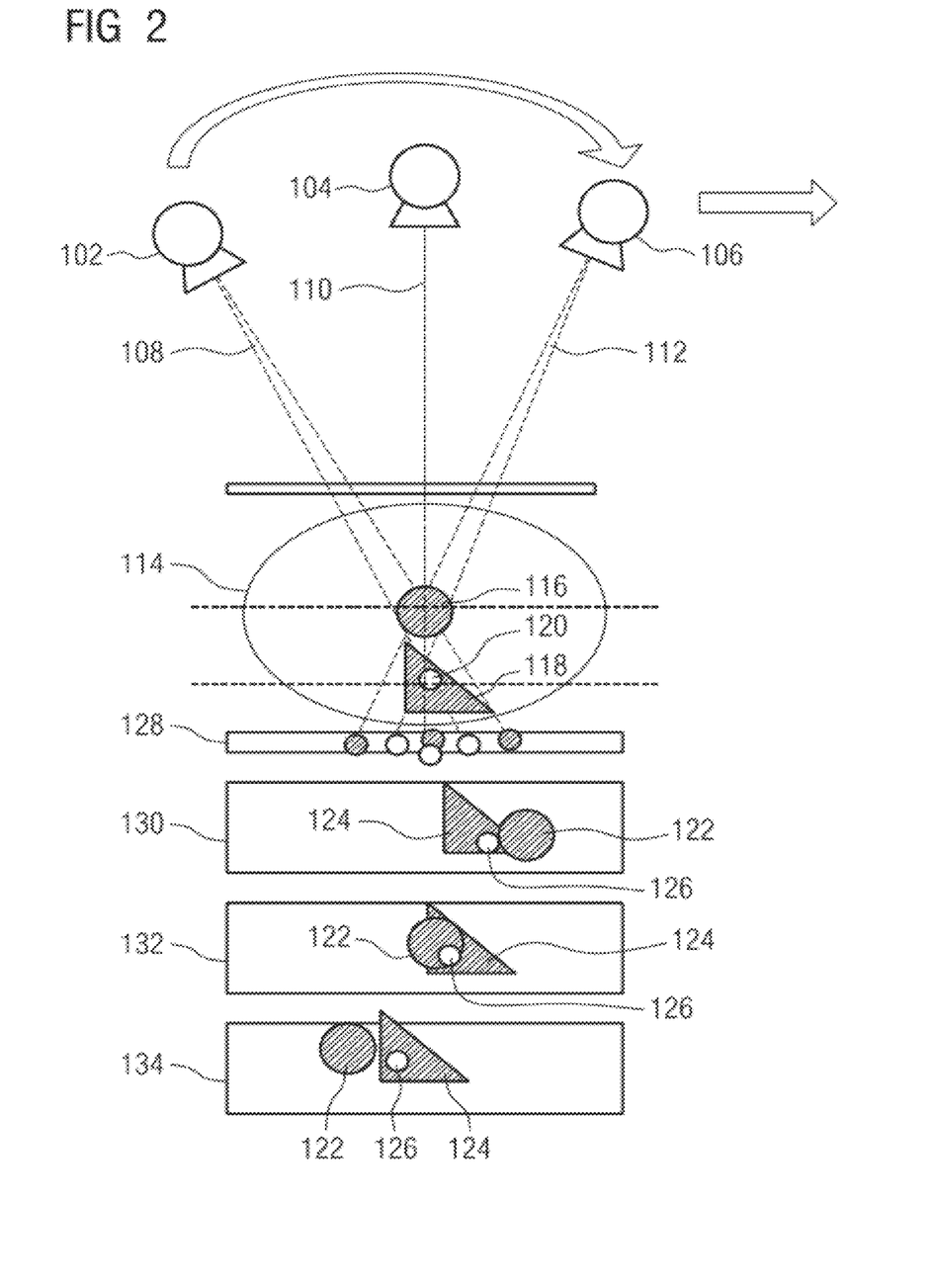
FIG. 2 is a schematic view showing a tomosynthesis being carried out.

The method for generating the projections is explained with reference to FIG. 2. A plurality of X-ray sources 102, 104, 106 are arranged over an angular range of approximately 50°. It is possible for 25 X-ray sources to be arranged, and so 25 projections can be generated. As an alternative to this, it is possible for an X-ray source to be pivoted over an angular range of 50° such that 25 projection recordings are generated. The first X-ray source 102 emits a first X-ray beam 108, which passes through the breast 114 and is attenuated by a first tissue region 116, a second tissue region 118 and a third tissue region 120. An X-ray detector 38 generates a first projection recording 130, in which the first tissue region image 122, the second tissue region image 124 and the third tissue region image 126 are in a first arrangement. The second X-ray beam source 104 emits a second X-ray beam 110, at a different angle, to the breast 114, the first tissue region 116, the second tissue region 118 and the third tissue region 120. These tissue regions are recorded by the second projection recording 132 and are in an arrangement that differs from that of the first slice recording 130. The third X-ray source 106 emits a third X-ray beam 112 to the breast at a further angle and this beam generates a third arrangement of the first tissue region image 122, second tissue region image 124 and third tissue region image 126 in the third projection recording 134.

Figure 3:
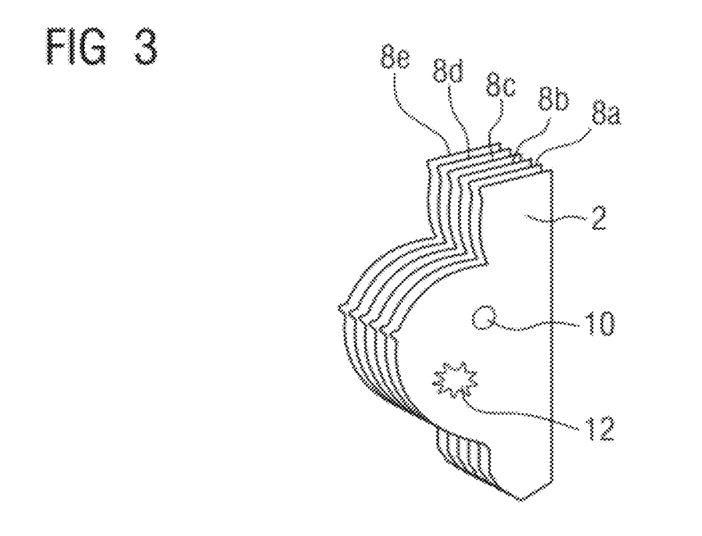
FIG. 3 schematically shows the shape of the breast emerging from the compression in the modality.

FIG. 3 shows the shape of the captured compressed breast, resulting from the compression, in the mediolateral oblique position. A plurality of slices 8a to 8e are shown. Furthermore, a first tissue change 10 and a second tissue change 12 are shown.

Figure 4:
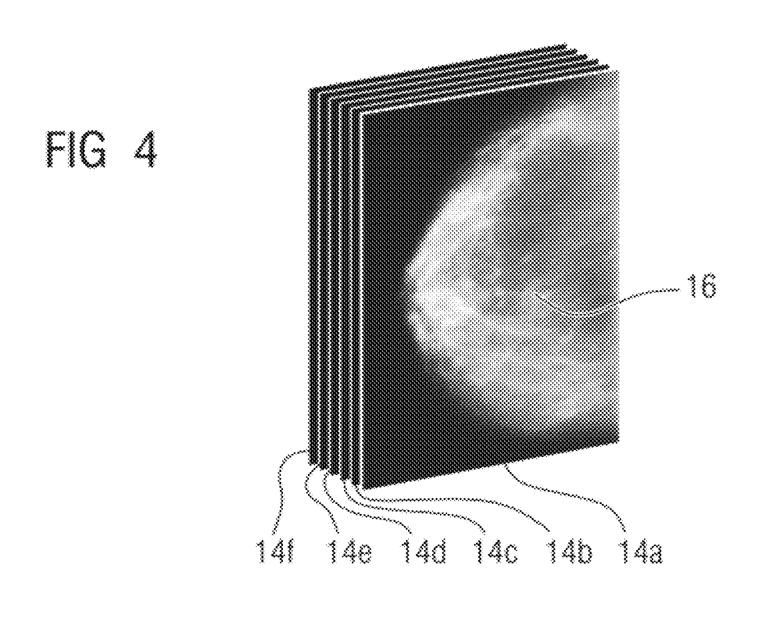
FIG. 4 shows slice images produced by means of DBT.

FIG. 4 shows a plurality of slice images, which were captured by means of the imaging modality, i.e. by means of DBT, and form the first image volume of the breast 16. A plurality of slice images 14a to 14f are shown. Since cancerous breast tissue has a similar attenuation coefficient to healthy tissue, it is difficult to assess whether cancerous tissue is present. This results in false positive or false negative diagnoses.

The functionality of the DBT-type modality was described at the outset and is known to a person skilled in the art from, for example, Imaging Systems for Medical Diagnostics, Arnulf Oppelt, Publicis Corporate Publishing, Erlangen, ISBN 3-89578-226-2; hence it is not described in any more detail, but the publication is incorporated herein by reference.

Figure 5:
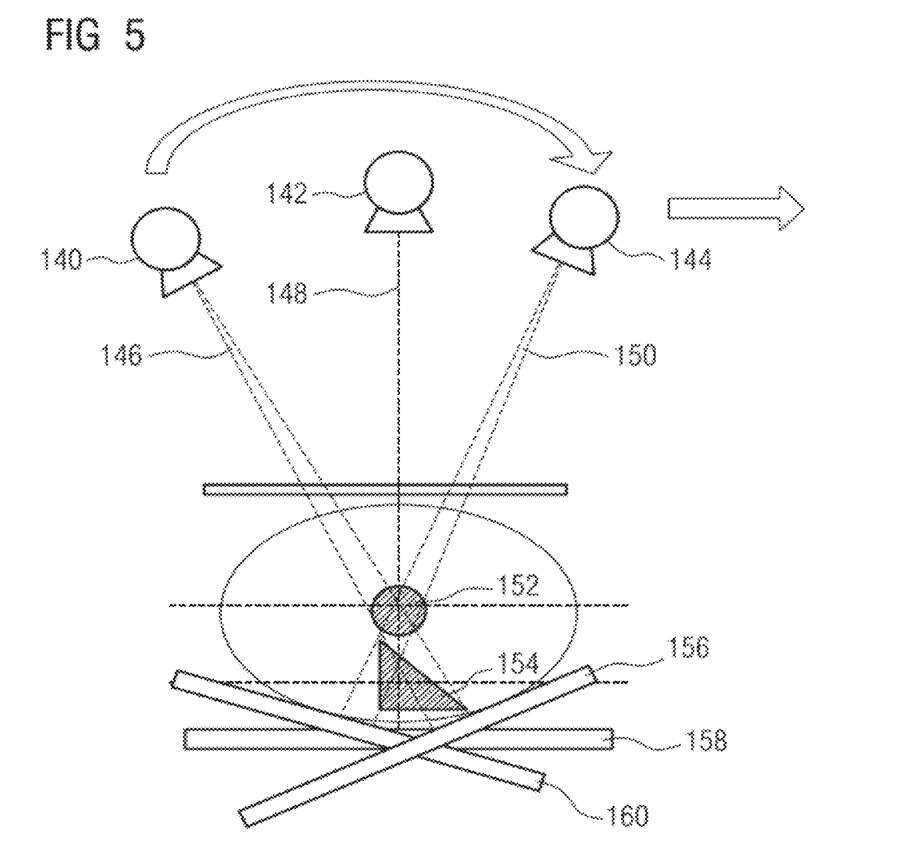
FIG. 5 shows the rotation of the tissue region.

The rotation of a slice image region corresponding to a partial tissue region is explained with reference to FIG. 5. Within the context of this disclosure, the term slice image portion should be understood such that this refers to the whole content of the slice images or part thereof.

The slice image region can be rotated such that virtual projection images are displayed, the latter being generated by a virtual X-ray source and a virtual detector.

A first virtual X-ray source 140 emits a first virtual X-ray beam 146, which passes through the first virtual tissue region 152 and the second virtual tissue region 154, and generates the first virtual projection 156. A second virtual X-ray source 142 generates a second virtual X-ray beam 148, which passes through the first virtual tissue region 152 and the second virtual tissue region 154, and generates a second virtual projection 158. Analogously to this, a third virtual X-ray source 144 generates a third virtual X-ray beam 150, which again is attenuated by the first virtual tissue region 152 and by the second tissue region 154 and which generates the third virtual projection recording 160.

The invention affords the possibility of showing to a radiologist projections from perspectives through which a real X-ray beam cannot pass.

The invention provides the radiologist with the option of generating virtual projections of the tissue. Furthermore, as a result of the rotating projections, the radiologist is able to select that projection that has the most amount of information for the respective diagnosis. The radiologist is put into a position where he or she is able to analyze the tissue changes from different directions, as a result of which false negative diagnoses and false positive diagnoses can be reduced.

The method according to the invention for generating rotating projections from DBT data as a rotating three-dimensional mammogram affords the possibility of obtaining the same amount of information as from FFDM (full field digital mammography) images. Furthermore, the three-dimensional information is kept and it becomes possible to remove or displace occlusions by rotating the three-dimensional mammogram. At the same time, all tissue densities and calcified structures or tissue changes are reconstructed simultaneously. The amount of images that have to be analyzed, transmitted and stored is reduced to a number of discrete observation angles, independently of the breast thickness. Moreover, originally recorded projections can be generated with a greater degree of detail, a better signal-to-noise ratio (SNR) and a higher contrast-to-noise ratio. This is achieved because every original projection is reconstructed by taking into account information from all recorded real projection recordings. The noise can be reduced as a result of the relatively large amount of image information.

The volume for visualizing the rotating mammogram can be generated from a set of forward projections of the reconstructed DBT volume. The forward projections can be calculated in advance for a set of sequential observation angles. The angular range of the rotating mammogram or the rotating projection recordings may, in terms of order of magnitude, approximately correspond to the maximum pivot angle of the real X-ray source when generating the real projection, as described above with reference to FIG. 2. Restricting the rotational angle for the three-dimensional mammogram is carried out in order to minimize the appearance of artifacts and more particularly so-called "out-of-plane" artifacts.

The projections of the rotating mammogram can be calculated from the DBT volume image using Siddon's method, Joseph's method, the distance driven projector, the "separable footprint" projector or a ray-casting method or another forward-projection technique. The resulting image sequence is stored as a set of images which comprise a DICOM (digital imaging and communications in medicine) format, a JPG format, a TIF format, a BMP format or another image format.

The volume comprising a sequence of optionally pre-calculated images is subsequently loaded into a computer so that it can be analyzed as a rotating three-dimensional mammogram using existing tools for analyzing volumes consisting of a plurality of slices. In the case of a rotating three-dimensional mammogram it is possible to use the same control elements that are used in the analysis of a conventional three-dimensional volume. The control elements then generate a rotating mammogram for the radiologist instead of showing the radiologist successive slices of a conventional three-dimensional volume.

The original DBT volume can be used within the same analysis procedure. The rotating three-dimensional mammogram can be displayed and used instead of the original DBT volume; this reduces the workload and reduces the number of images that have to be read, transmitted and stored.

Moreover, the rotating mammogram and the original DBT volume can be displayed at the same time. Furthermore, the DBT layers can be observed in sequence and the rotating three-dimensional mammogram is shown by a zoom window, should it be necessary, in order to subject a partial tissue region to a more detailed analysis. The zoom window can be determined by a mouse click.

However, it is also possible for the rotating three-dimensional mammogram to be observed in sequence and the conventional DBT layers to be shown by a zoom window that can be displayed by a mouse click.

Control elements can be provided for the user in order to navigate through the slices of the original volume image and/or the rotating three-dimensional mammogram during the analysis. Control elements can also be provided for the purpose of allowing the radiologist to be able to navigate when looking over the sequence of images of the underlying volume, i.e. the rotating three-dimensional mammogram, which is shown by the zoom window. Moreover, provision can be made for control elements for individually setting the windowing of the grayscale value range, for example for the original volume image, the image shown in the zoom window and/or the rotating three-dimensional mammogram. This can individually set the offset and the gradient of the grayscale value range selected by the window.

It is understood that the zoom window can have any shape; by way of example, the zoom window can be spherical, round, for example a cylinder orthogonal to the observation plane, conical or rectangular.

By way of example, the control elements can be operated by a conventional computer mouse, wherein the mouse can be used to define the zoom window. Furthermore, pop-up windows can be provided, which can be activated by means of the mouse buttons and by means of which the desired view can be selected. The direction in which the mouse is moved can determine which views are modified. By way of example, navigating through the slice recordings can be assigned to a vertical movement of the mouse and a horizontal movement of the mouse can rotate the mammogram. Moreover, scroll elements on the lower edge and/or on the side edge of the monitor display may be provided and these allow the radiologist to be able to navigate through the views.

The invention is advantageous in that it is possible to navigate through DBT data by visualizing a volume to be analyzed by means of a rotating three-dimensional mammogram. The rotating three-dimensional mammogram can have a set of forward projections of the reconstructed DBT volume. These forward projections can be calculated in advance for a set of successive observation angles. In terms of their order of magnitude, the observation angles approximately correspond to the maximum angular range when pivoting the real X-ray source for generating the real projections.

The expression rotating three-dimensional mammogram should be construed such that a mammogram is rotated virtually in the three-dimensional space. The rotating three-dimensional mammogram is stored as a series of snapshots at different angles. Use can be made of a standard format for storing the snapshots. As a result, the rotating three-dimensional mammogram can be displayed on any existing display apparatus or browser.

Figure 6:
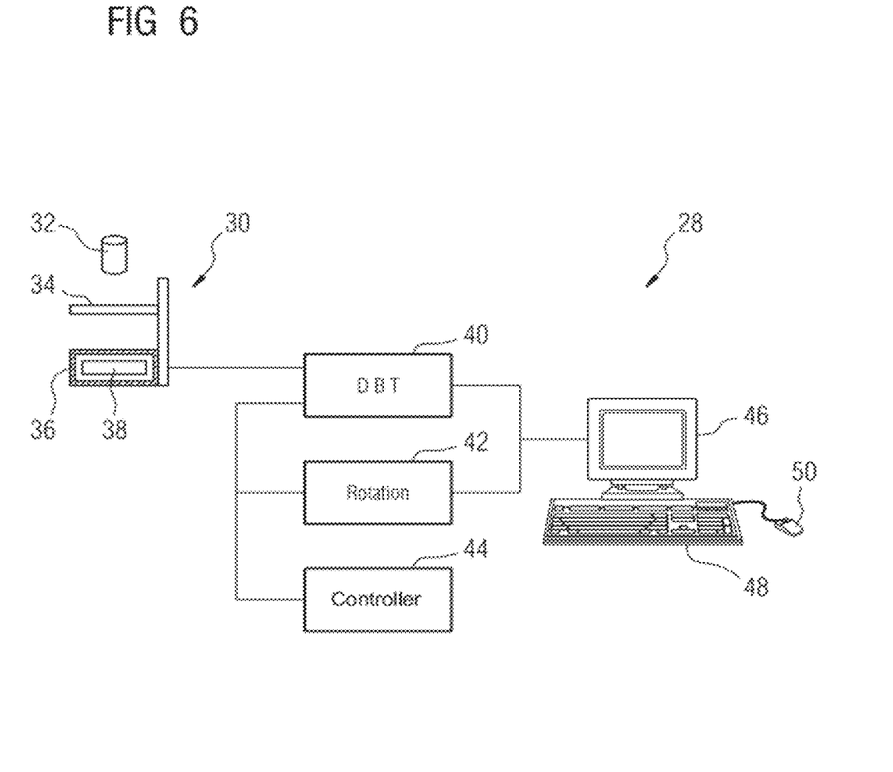
FIG. 6 shows an imaging system according to the invention.

FIG. 6 shows a medical system 28 for operation surroundings. The medical system 28 comprises an imaging modality 30 with an X-ray beam source 32, a compression plate 34, a compression table 36 and an X-ray detector 38. The X-ray source 32 can be pivotally mounted in order to generate projection recordings from different angles, which are captured by way of the X-ray detector 38.

The projections recorded by the X-ray detector 38 are transmitted to a DBT apparatus 40, where slice recordings are generated that are displayed on the display apparatus 46. A control apparatus 44 can, independently or in conjunction with the DBT apparatus 40, establish changed tissue, which is also displayed on the display apparatus 46. The changed tissue can have cancerous tissue, a carcinoma, a lump or any other medically relevant diagnosis. A radiologist can display the changed tissue by means of the input apparatus 48, 50 such that the diagnosis can be made as precisely as possible. The rotation apparatus 42 can rotate the image data of the breast generated by means of the DBT apparatus 40 and generate a rotating projection, wherein the rotating projection is displayed on the display apparatus 46. The control apparatus 44 controls the operation of both the DBT apparatus 40 and that of the rotation apparatus 42.

Finally, reference is made to the fact that the description of the invention and the exemplary embodiments should not, as a matter of principle, be understood as being restrictive in view of a particular physical implementation of the invention. More particularly, a person skilled in the art considers it obvious that the invention can be wholly or partly implemented as software and/or hardware, and/or can be implemented distributed over a plurality of physical products—more particularly also computer program products in this case.

The following list of reference numerals used in the above specification may aid the reader in reading the description:

2 Breast
4 Compression plate
6 Table
8 Slices
10 First tissue change
12 Second tissue change
14 Slice images
16 Breast
18 Breast
20 First tissue change
22 Second tissue change
28 Medical system
30 Modality
32 X-ray beam source
34 Compression plate
36 Compression table
38 X-ray detector
40 DBT apparatus
42 Transformation apparatus
44 Control apparatus
46 Display apparatus
50 Input apparatus
102 First X-ray source
104 Second X-ray source
106 Third X-ray source
108 First X-ray beam
110 Second X-ray beam
112 Third X-ray beam
114 Breast
116 First tissue region
118 Second tissue region
120 Third tissue region
122 First tissue region image
124 Second tissue region image
126 Third tissue region image
128 Detector element
130 First projection recording
132 Second projection recording
134 Third projection recording
140 First virtual X-ray source
142 Second virtual X-ray source
144 Third virtual X-ray source
146 First virtual X-ray beam
148 Second virtual X-ray beam
150 Third virtual X-ray beam
152 First virtual tissue region 154 Second virtual tissue region
156 First virtual projection recording
158 Second virtual projection recording
160 Third virtual projection recording

The invention claimed is:

1. An imaging method in digital breast tomosynthesis, which comprises the following steps:
   generating projection recordings of a breast tissue region by way of radiation emitted by an emitter, the radiation being captured by a detector after passing through the breast tissue region;
   generating slice images from the projection recordings; and
   performing a simulation in which only a portion of digital breast tomography data is rotated by rotating a slice image portion corresponding to a partial tissue region.

2. The imaging method according to claim 1, which comprises, for rotating the slice image portion, locating the rotational axis between the emitter and the detector.

3. The imaging method according to claim 1, wherein the step of generating slice images comprises carrying out a back projection.

4. The imaging method according to claim 1, wherein the step of rotating the slice image portion corresponding to a partial tissue region comprises carrying out a forward projection.

5. The imaging method according to claim 1, wherein the step of rotating the slice image portion corresponding to a partial tissue region comprises generating projection images.

6. The imaging method according to claim 5, wherein the step of rotating a slice image portion corresponding to a partial tissue region generates projection images by way of a simulated movement of one or both of the X-ray emitter and the X-ray detector.

7. The imaging method according to claim 1, wherein the step of rotating a slice image portion corresponding to a partial tissue region comprises substantially limiting a rotational angle to a rotational angle about which the X-ray emitter and/or the X-ray detector is pivoted during the step of generating the projection recordings of the tissue region.

8. The imaging method according to claim 1, which comprises selecting the slice image portion that should be rotated.

9. The imaging method according to claim 1, which comprises:
   rotating the slice image region over a range of discrete rotational angles for generating a set of rotation views;
   storing the set of rotation views in a memory; and
   reading a rotation view from the memory and displaying the rotation view.

10. A tomosynthesis mammography method, which comprises the following steps:
    emitting radiation by an emitter, causing the radiation to pass through a breast tissue region, and capturing the radiation by a detector after passing through the breast tissue region;
    generating projection recordings of the breast tissue region by the detector;
    generating slice images from the projection recordings; and
    performing a simulation in which only a portion of digital breast tomography data is rotated by rotating a slice image portion corresponding to a partial breast tissue region.

11. A rotation apparatus, configured to carry out the method according to claim 1.

12. An imaging system, comprising the rotation apparatus according to claim 11.

13. A computer program product, comprising computer-executable code in non-transitory form to be loaded into, or loaded in, a memory of a computer, and configured to carry out the steps of the method according to claim 1 upon being executed on the computer.

* * * * *